Figure 1:
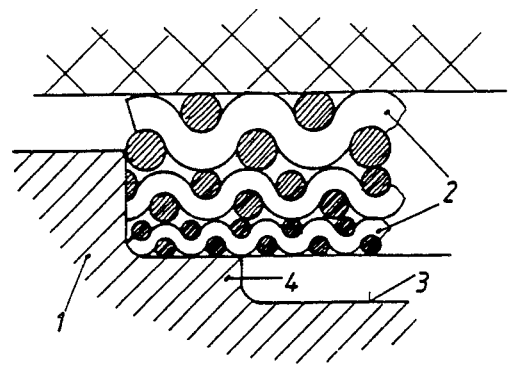

United States Patent

Koch et al.

[11] Patent Number: 4,969,904
[45] Date of Patent: Nov. 13, 1990

[54] BONE IMPLANT

[75] Inventors: Rudolf Koch, Berlingen, Switzerland; Erhard Heisig, Wangen/See, Fed. Rep. of Germany

[73] Assignee: Sulzer Brothers Limited, Winterthur, Switzerland

[21] Appl. No.: 308,244

[22] Filed: Feb. 8, 1989

[30] Foreign Application Priority Data

Feb. 26, 1988 [CH] Switzerland .......................... 719/88

[51] Int. Cl.$^5$ .............................................. A61F 00/00
[52] U.S. Cl. ...................................................... 623/16
[58] Field of Search ................................ 228/178, 193; 219/117.1; 623/20, 16, 22, 18, 23

[56] References Cited

U.S. PATENT DOCUMENTS

| | | | |
|---|---|---|---|
| 4,570,271 | 2/1986 | Sump | 623/16 |
| 4,636,219 | 1/1987 | Pratt et al. | 228/193 |
| 4,660,755 | 4/1987 | Farling et al. | 228/178 |
| 4,664,668 | 5/1987 | Beck et al. | 623/23 |
| 4,790,852 | 12/1988 | Noiles | 623/23 |
| 4,829,152 | 5/1989 | Rostoker et al. | 219/117.1 |

FOREIGN PATENT DOCUMENTS

| | | | |
|---|---|---|---|
| 8600970 | 4/1986 | Fed. Rep. of Germany . | |
| 2548533 | 11/1985 | France . | |
| 2142830 | 1/1985 | United Kingdom | 623/23 |

*Primary Examiner*—David J. Isabella
*Attorney, Agent, or Firm*—Kenyon & Kenyon

[57] ABSTRACT

The wire mesh is welded to the metal substrate via step-like protuberances formed on the outer surface of the substrate. The wire mesh is permanently deformed in the regions over the protuberances to facilitate forming of spot welds while the remainder of the mesh outside the zones of the protuberances remains porous for the intake of bone cement or the ingrowth of bone tissue.

11 Claims, 1 Drawing Sheet

BONE IMPLANT

This invention relates to a bone implant. More particularly, this invention relates to a bone implant construction.

Heretofore, various types of bone implants has been known. For example, U.S. Pat. No. 4,660,755 describes a bone implant, for example for use as a hip prosthesis, wherein a substrate material is adapted to transmit loads imparted to a skeletal structure while a porous surface is provided on the substrate to enhance biological fixation to a skeletal structure. In order to construct the implant, the substrate and porous layers are placed within a device whereby the porous layers may be tightly compacted toward the substrate while current from a current generator is conducted through the porous layers and substrate in order to generate sufficient heat to cause a surface metallurgical bonding between the porous layers as well as between the porous layers and the substrate.

European Patent Application 0189546 also describes a bone implant in which a metal substrate serves as a support for a multilayer braided and permanently deformable wire mesh having layers connected to one another and to the substrate by local weld zones.

French Patent 2548533 and German Gebrauchsmuster 8600970 describe bone implants using wire mesh structures which are secured to the substrate.

However, it has been found that fixing mesh layers to one another and to a substrate by spot welds at discrete places is expensive and difficult.

Accordingly, it is an object of the invention to simplify the fixation of a wire mesh to a metal substrate in the formation of a bone implant.

It is another object of the invention to improve the securement of a wire mesh to a metal substrate for a bone implant.

Briefly, the invention provides a bone implant which is comprised of a metal substrate having a plurality of steplike protuberances on an outer surface thereof and a multilayer metal wire mesh having permanently deformed sections welded to the protuberances with each section having layers of the mesh welded to each other therein.

The invention also provides a method of securing a multilayer metal wire mesh to a metal substrate which includes the steps of providing a substrate with a plurality of step-like protuberances on an outer surface, positioning a multilayer metal mesh over the surface and protuberances of the substrate, pressing the mesh against the substrate to permanently deform the sections of the mesh which are disposed over the protuberances without permanently deforming the remainder of the mesh and welding the permanently deformed sections to the protuberances and the layers of the deformed sections to each other. In accordance with the method, the pressing of the mesh against the substrate and the welding of the permanently deformed sections are performed simultaneously and produce spot welds between the mesh layers and between the protuberances and the deformed sections of mesh.

When the wire mesh is pressed onto the substrate, the layers of the mesh adapt to the contour of the substrate by permanent deformation. However, in the remaining regions of the substrate surface, there is only slight, if any, compression of the mesh structure. Because the discrete layers of the mesh experience substantial changes in shape and substantial compression over the protuberances of the substrate, a relatively large contact area is formed between the substrate and the mesh as well as between the individual mesh layers. Consequently, welding of these layers, for example, using spot-welding electrodes permits the electrodes to encounter an adequate metal bridge along which a "strand" of liquid metal is produced. This strand subsequently hardens into a weld joint to secure the contiguous layers of the mesh together as well as the mesh to the protuberances. Advantageously, the spot-welding electrodes may be disposed in zones of a mesh-compressing ram used for the pressing of the mesh against the substrate.

Figure 2:
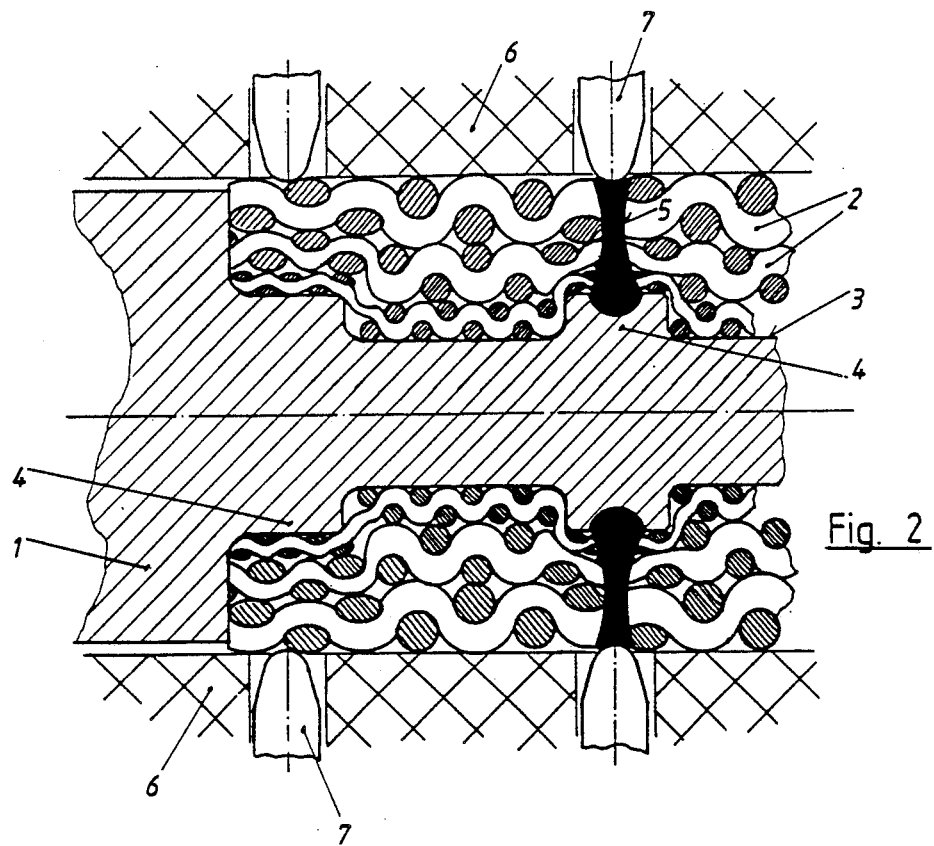

These and other objects and advantages of the invention will become more apparent from the folloWing detailed description taken in conjunction with the accompanying drawings wherein:

FIG. 1 diagrammatically illustrates a cross sectional view of a wire mesh in position for pressing against a substrate by a ram: and FIG. 2 illustrates a cross sectional view of wire mesh being pressed and welded to a substrate in accordance with the invention.

Referring to FIG. 1, the bone implant is to be formed of a metal substrate 1, for example, a metal shank for a hip joint prosthesis, and a multilayer metal wire mesh 2.

The mesh 2 is in the form of a number of layers, the mesh size of which differ and decrease from the outside toward the inside.

In order to receive the mesh 2, the substrate 1 has a stepped cross-section wherein the innermost surface provides a accessed foundation surface 3 for the mesh 2. In addition, a plurality of step-like protuberances 4 project from the foundation surface 3 and are disposed at places where the wire mesh 2 is to be connected to the substrate 1 by spot welds 5 as indicated in FIG. 2 as well as where the mesh layers are to be connected to one another.

Referring to FIG. 2, the substrate 1 may be in form of a shank while the wire mesh 2 is disposed over opposite sides of the substrate !. In addition, the protuberances 4 are spaced along the foundation surface 3 which acts as an outer surface of the substrate 1. In order to secure the mesh 2 to the substrate 1, the mesh 2 is pressed against the substrate 1 by means of a ram 6 in which welding electrodes 7 are disposed. Upon pressing of the mesh 2 against the substrate 1, the sections of the mesh 2 disposed over the protuberances 4 permanently deform substantially without permanent deformation of the remainder of the mesh 2. That is, only slight compression substantially without permanent deformation occurs in the zones of the foundation surface 3 between the protuberances 4. Consequently, adequately compressed material for the formation of spot welds 5 is available while, on the other hand, the porosity of the mesh 2 which assists the ingrowth of bone tissue or the taking in of bone cement is not excessively impaired.

During pressing in of the mesh, the welding electrode 7 may be activated to generate a current sufficient to form spot welds 5 between the individual layers of the mesh 2 as well as between the mesh 2 and the protuberances 4 of the substrate 1 In this respect, the position of the protuberances 4 and the position of the electrodes 7 are coordinated with one another so that the welds occur as spot welds 5 on the protuberances 4.

As indicated in FIG. 2, where the substrate 1 forms a shank of a hip joint implant, the mesh 2 may be disposed on opposite sides of the shank. In this respect, the mesh may be applied as individual layers only to two opposite sides of the shank or may be in the form of a mesh which is circumferentially disposed around the shank.

Of course, the substrate may be of any other shape and construction to receive a wire mesh for use other than as a shank.

The invention thus provides a bone implant wherein a multilayer metal wire mesh is securely fixed to a substrate in a secure manner while providing sufficient porosity for the ingrowth of bone tissue for implantation in a bone cement bed.

The invention further provides a technique for easily securing a metal wire mesh to a metal substrate. In this respect, the compression and permanent deformation of the wire mesh at the protuberances of the substrate produces accumulations of material which facilitate the production of a spot weld.

What is claimed is:

1. A bone implant comprising
   a metal substrate having a plurality of spaced-apart protuberances on an outer surface thereof;
   a multilayer metal wire mesh disposed over said outer surface, said mesh having compressed sections disposed over said protuberances; and
   spot welds securing said compressed sections of said mesh to said protuberances and said layers in said compressed sections to each other.

2. A bone implant as set forth in claim 1 wherein said substrate is a shank having said step-like protuberances on at least two opposite sides.

3. A bone implant as set forth in claim 2 wherein said mesh is circumferentially disposed around said shank.

4. A bone implant comprising
   a metal substrate having a plurality of spaced apart protuberances on an outer surface thereof;
   a multilayer metal wire mesh disposed over said surface and said projections, said mesh having compressed sections disposed over said protuberances and uncompressed sections disposed over said surface between said protuberances; and
   spot welds securing said compressed sections of said mesh to said protuberances and said layers in said compressed sections to each other.

5. A bone implant as set forth in claim 4 wherein said substrate is a shank having said protuberances on at least two opposite sides.

6. A bone implant as set forth in claim 5 wherein said mesh is circumferentially disposed around said shank.

7. A bone implant as set forth in claim 4 wherein said mesh has layers of increasing mesh size outwardly of said substrate surface.

8. A bone implant as set forth in claim 4 wherein said compressed sections of said mesh are permanently deformed.

9. A bone implant comprising
   a metal substrate having a recessed outer surface and a plurality of spaced apart protuberances on said outer surfaces;
   a multilayer metal wire mesh disposed over said surface and said projections, said mesh having compressed sections disposed over said protuberances and uncompressed sections disposed over an in contact with said surface between said protuberances for the ingrowth of bone tissue into said uncompressed sections; and
   spot welds securing said compressed sections of said mesh to said protuberances and individual layers in said compressed sections to each other.

10. A bone implant as set forth in claim 9 wherein said mesh is circumferentially disposed around said substrate.

11. A bone implant as set forth in claim 10 wherein said mesh has layers of increasing mesh size outwardly of said substrate surface.

* * * * *

UNITED STATES PATENT AND TRADEMARK OFFICE
CERTIFICATE OF CORRECTION

PATENT NO. : 4,969,904

DATED : November 13, 1990

INVENTOR(S) : RUDOLF KOCH, et al

It is certified that error appears in the above-identified patent and that said Letters Patent is hereby corrected as shown below:

```
Column 2, line 16 change "folloWing" to -following-
Column 2, line 21 change "ram:" to -ram;-
Column 2, line 33 change "accessed" to -recessed-
Column 2, line 42 change "substrate!. In" to -substrate 1. In-
Column 2, line 63 change "1 In" to -1.  In-
Column 4, line 25 change "an" to -and-
```

Signed and Sealed this

Thirtieth Day of June, 1992

*Attest:*

DOUGLAS B. COMER

*Attesting Officer*   *Acting Commissioner of Patents and Trademarks*